United States Patent [19]
Peter

[11] Patent Number: 5,917,878
[45] Date of Patent: Jun. 29, 1999

[54] MEASUREMENT SYSTEM FOR A COMPUTED TOMOGRAPHY APPARATUS

[75] Inventor: Fritz Peter, Spardorf, Germany

[73] Assignee: Siemens Aktiengesellschaft, Munich, Germany

[21] Appl. No.: 08/948,333

[22] Filed: Oct. 10, 1997

[30] Foreign Application Priority Data

Nov. 12, 1996 [DE] Germany ............................ 196 46 699
Jun. 26, 1997 [DE] Germany ............................ 197 72 719

[51] Int. Cl.$^6$ ................................................. G01N 23/00
[52] U.S. Cl. ................................................. 378/19; 378/4
[58] Field of Search ..................... 378/19, 4; 250/370.09

[56] References Cited

U.S. PATENT DOCUMENTS

| | | |
|---|---|---|
| 4,338,521 | 7/1982 | Shaw et al. ...................... 250/370.09 |
| 4,571,495 | 2/1986 | Distler et al. . |
| 5,592,523 | 1/1997 | Tuy et al. ................................. 378/19 |

*Primary Examiner*—Craig E. Church
*Attorney, Agent, or Firm*—Hill & Simpson

[57] ABSTRACT

The individual detector elements of an X-ray detector in a computed tomography apparatus are mounted on a formed part composed of insulator material, on whose surface interconnects are applied that electrically connect the outputs of the individual detector elements to electronics components. The formed part is angled when viewed from the side.

4 Claims, 2 Drawing Sheets

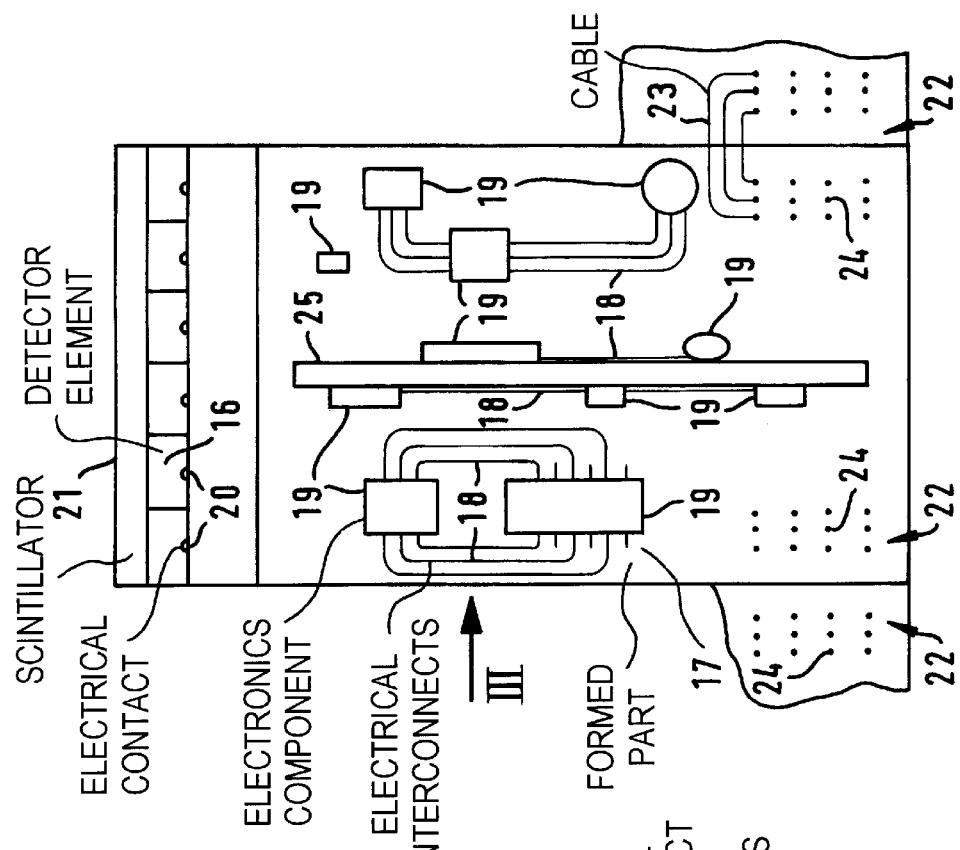
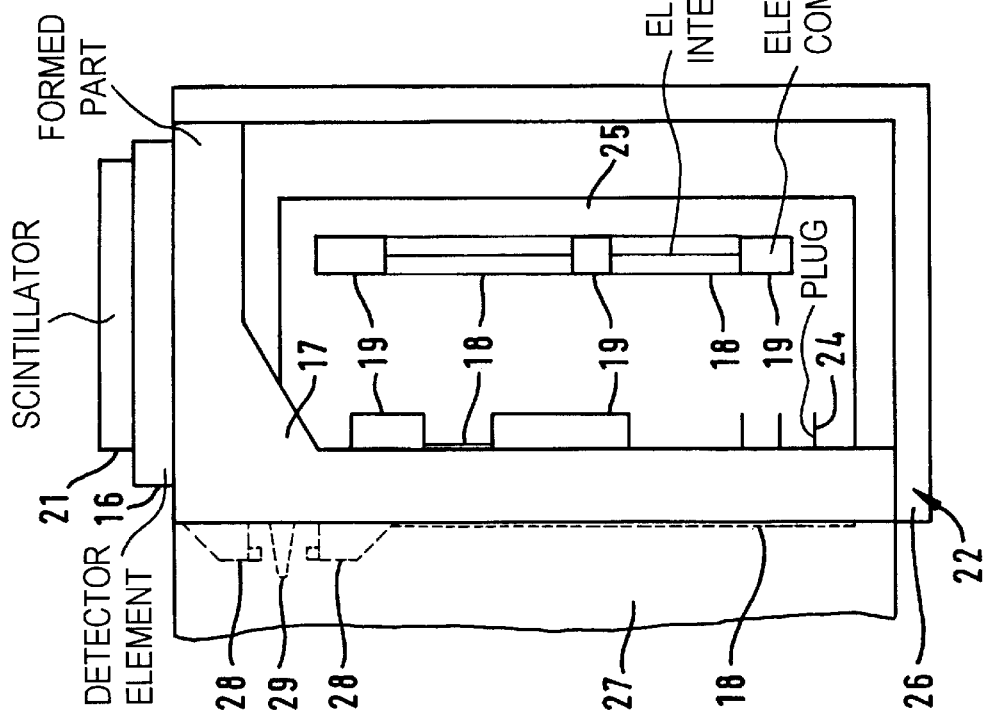

MEASUREMENT SYSTEM FOR A COMPUTED TOMOGRAPHY APPARATUS

BACKGROUND OF THE INVENTION

1. Field of the Invention

The present invention is directed to a measurement system for a computed tomography apparatus, and more specifically to an improvement in the detector structure for such a measurement system.

2. Description of the Prior Art

A computed tomography apparatus is known that has a carrier plate on which the detector elements for the registering incident X-rays and electronics boards for processing the detector signals are mounted. The carrier plate is implemented as a printed circuit board and the measurement system is held in a frame (U.S. Pat. No. 4,571,495).

SUMMARY OF THE INVENTION

An object of the present invention is to provide a structurally simplified measurement system for a computed tomography apparatus compared to known systems.

The above object is achieved in accordance with the principles of the present invention in a measurement system for a computed tomography apparatus having a radiation detector composed of a number of individual detector elements, the detector elements being attached to a formed part composed of insulator material. The formed part carries interconnects on its surface which electrically connect the individual detector elements to electronics components. The electronics components are disposed directly on the surface of the formed part. The formed part thus simultaneously serves as a structural frame for the radiation receiver as well as the sole carrier for all of the electrical interconnects for producing the necessary electrical connections between the detector elements and the electronics components.

In the inventive measurement system, a formed part composed of insulator material is used that has a number of functions. This formed part carries the detector elements and electronic components for processing the detector signals, i.e. serves for mounting the detector elements and the channel electronics. The need for a separate frame for the overall measurement system is eliminated. On its surface, the formed part of insulator material has electrical interconnects for electrically connecting the individual components.

DESCRIPTION OF THE DRAWINGS

FIG. 2 is a detailed view of a radiation detector constructed in accordance with the principles of the present invention, for use in the computed tomography apparatus of FIG. 1.

FIG. 3 is a view of the inventive radiation detector, as seen in the direction of the arrow III in FIG. 2.

DESCRIPTION OF THE PREFERRED EMBODIMENTS

Figure 1:
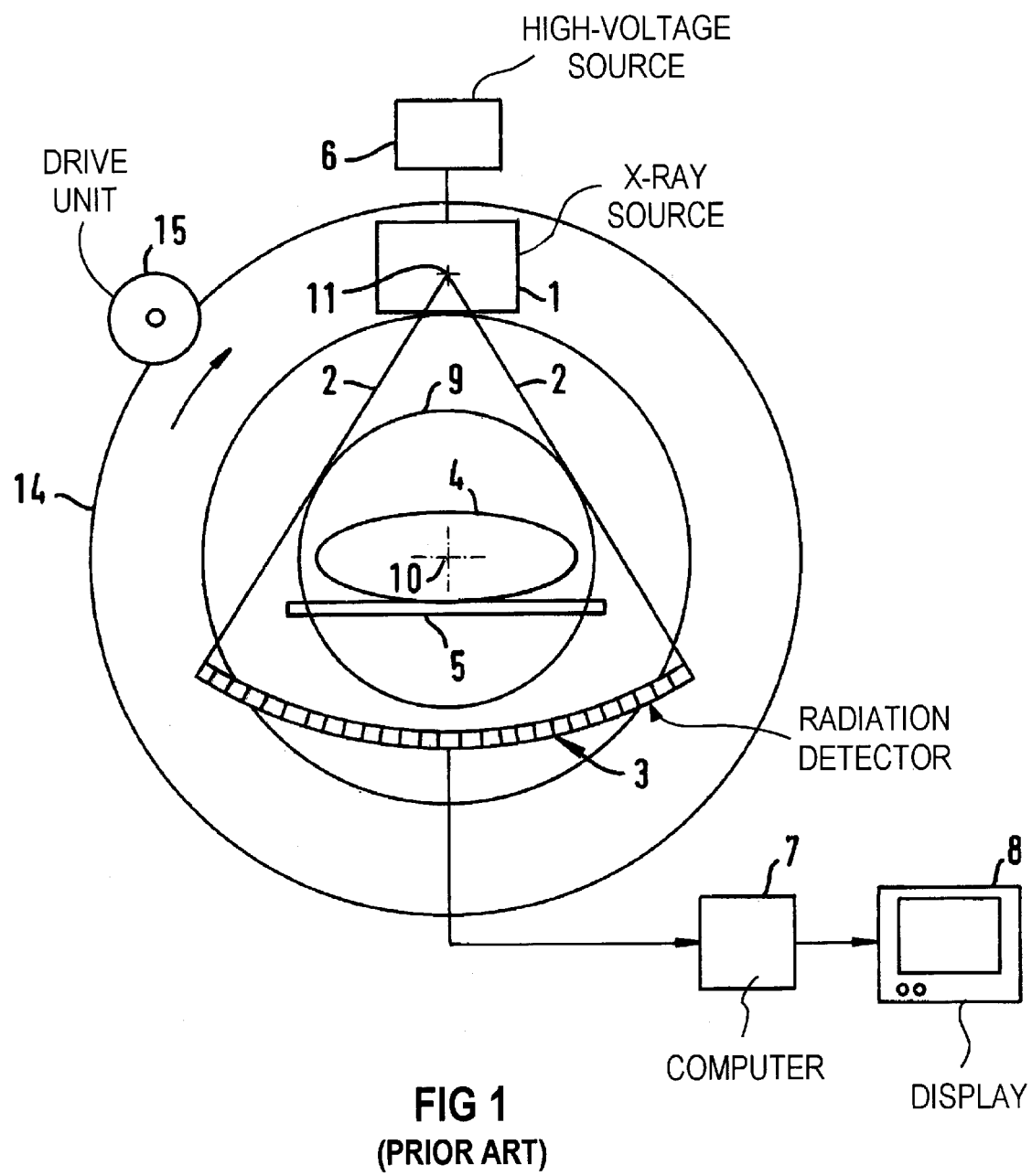
FIG. 1 shows the basic components of a known X-ray computed tomography apparatus for explaining the invention.

The computed tomography apparatus shown in FIG. 1 has a measurement unit composed of an X-ray source 1 that emits a fan-shaped X-ray beam 2 and of a radiation detector 3 that is composed of a number of individual detector elements, for example a row or rows of 512 individual detector elements. The X-ray beam focus is referenced 11. The patient 4 to be examined lies on a patient bed 5. For scanning the patient 4, the measurement unit carrying the X-ray source 1, and the detector 3 is rotated through 360° around the measurement field 9 in which the patient 4 lies. The rotational axis is referenced 10. The X-ray source 1, which is supplied from a high voltage source 6, can be operated to emit pulsed or continuous radiation. Sets of data are generated at predetermined angular positions of the measurement unit, these sets of data being supplied from the radiation receiver 3 to a computer 7 that calculates the attenuation coefficients of predetermined picture elements from the generated datasets in a known manner and visually reproduces them on a display 8. Accordingly, an image of the transirradiated slice of the patient appears on the display 8.

FIG. 1 also shows a gantry 14 on which the X-ray source 1 and the radiation receiver 3 are seated. The rotation of the X-ray source 1 and the X-ray beam 2 ensues by means of a drive unit 15 which engages the gantry 14.

The radiation receiver 3 is only schematically shown in FIG. 1. FIGS. 2 and 3 show its structure in greater detail. As can be seen in FIG. 2 a number of individual detector elements 16 is mounted on a formed part 17 composed of insulator material such as plastic, preferably as an injection molded part. Surface interconnects 18 are applied on both sides (surfaces) of the part 17. Detector arrays can also be provided. Electronics components 19 (for example, ICs) are also mounted on the formed part 17, these being electrically connected to one another by the interconnects 18. The individual detector elements 16 are also electrically connected to the electronics components 19 by the interconnects 18 on the formed part 17. The formed part 17, accordingly, serves for holding the detector elements 16 and the components 19 as well as for making their electrical connections.

As can be seen from FIGS. 1 and 3, the radiation receiver 3 is subdivided into individual detectors transversely relative to the rotational axis 10 as well as in the direction thereof, so that simultaneous scanning of a number of slices of the patient 4 is enabled. The individual detector elements 16 are placed in electrical contact with the interconnects 18 on the formed part 17 by means of contacts 20. Each individual detector element 16 is preceded by a scintillator 21 for converting the incident X-rays into visible light, which the individual detector elements 16 fashioned as semiconductor photodetectors convert into corresponding electrical signals.

As shown in FIG. 2, the radiation receiver 3 is constructed of a number of modules 22, each module comprising a formed part 17 with the detector elements 16 and the components 19. Sixteen individual detector elements 16, for example, can be provided per module 22, with a total number of, for example, 512 individual detector elements corresponding to a total number of 32 modules 22. The modules 22 can be electrically connected to one another via cables 23 that are respectively connected to injection-molded plug devices 24.

FIG. 3 is a view in the direction of the arrow III in FIG. 2, showing that the formed part 17 is angled, so that the individual detector elements 16 lie at the outside on the upper leg and the electronics components 19 lie in the inside of the angle. This upper leg and the other leg form a non-zero angle, preferably a 90° angle. Some of the electronics components 19 are arranged on an inwardly slanting projection 25. The angle is thereby closed by a covering 26, so that a profile having a box-shaped overall cross-section is produced for the acceptance of the electronics components 19. A carrier plate 27 carries the modules 22 with the assistance of catch noses 28. A fit pin 29 serves for the alignment of the formed part 17 relative to the focus 11 of the X-ray source 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. In a measurement system for a computed tomography apparatus, the measurement system comprising a radiation source and a radiation receiver rotatable around an examination volume, the improvement of said radiation receiver comprising:

a plurality of individual radiation detector elements;

a plurality of electronics components operable in combination with said individual detector elements;

a formed part, composed of insulator material, said formed part having first and second legs disposed at a non-zero angle relative to each other, said first and second legs forming an interior of said formed part, and said individual detector elements being mounted on said first leg and said electronics components being mounted in said interior of said formed part, and said formed part having a surface; and a plurality of electrical interconnects on said surface of said formed part respectively electrically interconnecting said individual detector elements and said electronics components, said formed part comprising a frame and a sole carrier for said electrical interconnects and for mounting said individual detector elements and said electronics components.

2. The improvement of claim 1 wherein said formed part comprises a plurality of formed part segments joined to each other.

3. The improvement of claim 2 wherein each formed part segment carries a portion of said plurality of electrical components thereon, and wherein each formed part segment has a plug, electrically connected to the portion of said plurality of electrical components carried thereon.

4. The improvement of claim 1 further comprising an angled covering connected to said formed part and forming, in combination with said formed part, an arrangement having a box-shaped cross-section.

\* \* \* \* \*